United States Patent
Sato et al.

(10) Patent No.: US 11,292,752 B2
(45) Date of Patent: Apr. 5, 2022

(54) METHOD FOR PRODUCING ALDEHYDE AND METHOD FOR PRODUCING ALCOHOL

(71) Applicant: Mitsubishi Chemical Corporation, Chiyoda-ku (JP)

(72) Inventors: Takashi Sato, Tokyo (JP); Yoshiyuki Tanaka, Tokyo (JP)

(73) Assignee: Mitsubishi Chemical Corporation, Chiyoda-ku (JP)

( * ) Notice: Subject to any disclaimer, the term of this patent is extended or adjusted under 35 U.S.C. 154(b) by 0 days.

(21) Appl. No.: 16/871,098

(22) Filed: May 11, 2020

(65) Prior Publication Data

US 2020/0270186 A1    Aug. 27, 2020

Related U.S. Application Data

(63) Continuation of application No. PCT/JP2018/042160, filed on Nov. 14, 2018.

(30) Foreign Application Priority Data

Nov. 15, 2017   (JP) .............................. JP2017-219776

(51) Int. Cl.
| | |
|---|---|
| *C07C 45/50* | (2006.01) |
| *C07B 41/00* | (2006.01) |
| *C07B 41/06* | (2006.01) |
| *C07B 63/04* | (2006.01) |
| *C07B 41/02* | (2006.01) |

(52) U.S. Cl.
CPC .............. *C07B 41/06* (2013.01); *C07B 41/02* (2013.01); *C07B 63/04* (2013.01); *C07B 2200/13* (2013.01)

(58) Field of Classification Search
CPC .......... C07C 45/50; C07B 41/06; C07B 41/02
See application file for complete search history.

(56) References Cited

U.S. PATENT DOCUMENTS

| | | | |
|---|---|---|---|
| 4,396,551 A | 8/1983 | Tsunoda et al. | |
| 4,473,655 A | 9/1984 | Tsunoda et al. | |
| 4,528,403 A | 7/1985 | Tano et al. | |
| 4,605,708 A | 8/1986 | Billig et al. | |
| 4,822,917 A | 4/1989 | Miyazawa et al. | |
| 5,463,146 A | 10/1995 | Slaugh et al. | |
| 5,545,767 A | 8/1996 | Weider et al. | |
| 5,563,302 A | 10/1996 | Weider et al. | |
| 5,576,471 A | 11/1996 | Semple et al. | |
| 5,585,528 A | 12/1996 | Powell et al. | |
| 5,684,214 A | 11/1997 | Weider et al. | |
| 5,689,016 A | 11/1997 | Weider et al. | |
| 5,770,776 A | 6/1998 | Powell et al. | |
| 5,777,182 A | 7/1998 | Powell et al. | |
| 5,981,808 A | 11/1999 | Powell et al. | |
| 2003/0175188 A1 | 9/2003 | Gelling et al. | |
| 2004/0171478 A1 | 9/2004 | Crabtree et al. | |
| 2004/0186323 A1 | 9/2004 | Banister et al. | |
| 2005/0209489 A1 | 9/2005 | Moller et al. | |
| 2012/0130102 A1 | 5/2012 | Crabtree et al. | |

FOREIGN PATENT DOCUMENTS

| | | |
|---|---|---|
| EP | WO-A2-02-96846 | 3/2021 |
| GB | A-2092907 | 6/1982 |
| JP | 57-072995 A | 5/1982 |
| JP | 57-087845 A | 6/1982 |
| JP | 57-122948 A | 7/1982 |
| JP | 59-076034 A | 4/1984 |
| JP | 63-264433 A | 11/1988 |
| JP | 09-094461 A | 4/1997 |
| JP | 10-507747 A | 7/1998 |
| JP | 2000-325802 A | 11/2000 |
| JP | 2004-503380 A | 2/2004 |
| JP | 2004-526570 A | 9/2004 |
| JP | 2004-534044 A | 11/2004 |
| JP | 2006-151826 A | 6/2006 |
| RU | 952835 | 8/1982 |
| WO | WO 96/10552 A1 | 4/1996 |

OTHER PUBLICATIONS

International Search Report dated Jan. 29, 2019 in PCT/JP2018/042160 filed on Nov. 14, 2018, citing documents AA-AB, AF-AH, AN, AR-AV, BE, & BO therein, (with English Translation), 5 pages.
GCC OA GC 2018-36473 on Feb. 5, 2020 (with English Translation), 5 pages.
GCC Office Action dated Nov. 16, 2020 in GCC Patent Application No. GC 2018-36473 (with English language translation), 8 pages.
EP-EESR 1887879.9 dated on Mar. 19, 2021, 8 pages.
Office Action as received in the corresponding RU patent application No. 2020115799(025953) dated Dec. 20, 2021 w/English Translation, 21 pages.

*Primary Examiner* — Sikarl A Witherspoon
(74) *Attorney, Agent, or Firm* — Oblon, McClelland, Maier & Neustadt, L.L.P.

(57) ABSTRACT

The present invention relates to a method for producing an aldehyde by a hydroformylation reaction of reacting an olefin with hydrogen and carbon monoxide in the presence of a Group 8 to 10 metal-phosphine complex catalyst, including the following steps (1) and (2): (1) a step of oxidizing by withdrawing a reaction solution having accumulated therein a high-boiling-point byproduct from a reaction zone and bringing the withdrawn reaction solution into contact with an oxygen-containing gas, and (2) a step of, after the step (1), mixing a poor solvent and hydrogen with the reaction solution, then crystallizing the Group 8 to 10 metal-phosphine complex catalyst by crystallization, and recovering the crystallized complex catalyst from the reaction solution.

12 Claims, 1 Drawing Sheet

METHOD FOR PRODUCING ALDEHYDE AND METHOD FOR PRODUCING ALCOHOL

TECHNICAL FIELD

The present invention relates to a method for producing an aldehyde. More specifically, the present invention relates to a method for producing an aldehyde by reacting an olefin with hydrogen and carbon monoxide in the presence of a Group 8 to 10 metal-phosphine complex catalyst such as rhodium-phosphine complex catalyst.

Additionally, the present invention relates to a method for producing alcohol using aldehyde produced by the above production method of aldehyde.

BACKGROUND ART

As a method for producing an aldehyde, there is a method for producing an aldehyde by hydroformylating an olefin with hydrogen and carbon monoxide in the presence of a Group 8 to 10 metal-phosphine complex catalyst.

The catalyst used for the hydroformylation reaction of an olefin contains an expensive Group 8 to 10 metal such as rhodium, and it is therefore ideal to use the catalyst semi-permanently. Accordingly, a method in which the reaction product is separated from the reaction solution and the reaction solution containing the catalyst as a distillation residue is circulated to a reaction zone and reused, or a method in which the reaction product is distilled off and separated from a reaction zone by using gas stripping and the reaction is continuously performed while allowing the catalyst-containing reaction solution to remain in the reaction zone, is employed.

However, in the hydroformylation reaction, a high-boiling-point byproduct such as aldehyde condensation byproduct is produced and accumulated, making it necessary to withdraw part of the reaction solution continuously or intermittently outside the reaction zone. Since the withdrawn reaction solution contains the catalyst, in addition to the high-boiling-point byproduct, a method for recovering it is proposed.

For example, Patent Documents 1 and 2 describe a method in which a hydroformylation reaction solution having accumulated therein a high-boiling-point byproduct is mixed with an alcohol, water and hydrogen, thereby precipitating and recovering a hydrogen-coordinated rhodium-phosphine complex catalyst.

Patent Document 3 describes a method for recovering, in which a hydroformylation reaction solution containing a Group 8 metal complex using, as a ligand, a tertiary organophosphorus compound such as triphenylphosphine is put into contact with an oxidizing agent in the presence of a free tertiary organophosphorus compound, a polar organic solvent, water and a basic substance to precipitate a solid complex of a Group 8 metal.

Furthermore, Patent Document 4 discloses a method in which an alkyl phosphine produced by partially substituting a ligand such as triarylphosphine with an alkyl group of α-olefin is treated with an oxygen gas and converted to its corresponding phosphine oxide and the deactivated catalyst is thereby reactivated.

BACKGROUND ART LITERATURE

Patent Document

[Patent Document 1] JP-A-S57-122948
[Patent Document 2] JP-A-2006-151826
[Patent Document 3] JP-A-S57-72995
[Patent Document 4] JP-A-S57-87845

SUMMARY OF THE INVENTION

Problems to be Solved by the Invention

However, according to the methods described in the Patent Document 1 and Patent Document 2, the complex catalyst could not be sufficiently recovered by these methods. Additionally, according to the method described in the Patent Document 3, since a basic substance is used, there is a problem that, for example, a washing or neutralization operation for removing the basic substance is necessary before returning a solid complex to a reaction zone and reusing and the process becomes cumbersome. Furthermore, according to the method described in the Patent Document 4, a highly active complex catalyst could not be satisfactorily recovered even by this method.

An object of the present invention is to provide a method for producing an aldehyde wherein a highly active complex catalyst from a reaction solution which is withdrawn outside a reaction zone so as to prevent accumulation of a high-boiling-point byproduct is efficiently recovered.

Means for Solving the Problems

As a result of intensive studies in consideration of the object above, the present inventors have found that when the reaction solution after hydroformylation reaction is oxidized and furthermore, the reaction solution is treated using a poor solvent and hydrogen, a highly active complex catalyst can be efficiently recovered in high yield. The present invention has been accomplished based on this finding.

More specifically, the gist of the present invention resides in the following [1] to [14].

[1] A method for producing an aldehyde by a hydroformylation reaction of reacting an olefin with hydrogen and carbon monoxide in the presence of a Group 8 to 10 metal-phosphine complex catalyst, containing the following steps (1) and (2):

(1) a step of withdrawing a reaction solution having accumulated therein a high-boiling-point byproduct from a reaction zone and oxidizing by bringing the withdrawn reaction solution into contact with an oxygen-containing gas, and (2) a step of, after the step (1), (2-1) mixing a poor solvent and hydrogen with the reaction solution, (2-2) then crystallizing the Group 8 to 10 metal-phosphine complex catalyst by crystallization, and (2-3) recovering the crystallized complex catalyst from the reaction solution.

[2] The aldehyde production method according to [1], wherein in the oxidation, an alkyl-substituted phosphine in the reaction solution is converted to an alkyl-substituted phosphine oxide.

[3] The aldehyde production method according to [1] or [2], wherein in the oxidation, a cluster complex in the reaction solution is decomposed.

[4] The aldehyde production method according to [2], wherein an oxidation ratio of the alkyl-substituted phosphine is from 5 to 80%.

[5] The aldehyde production method according to any one of [1] to [4], wherein the oxygen-containing gas is at least one selected from the group consisting of oxygen, air, and a gas obtained by adding nitrogen to air.

[6] The aldehyde production method according to any one of [1] to [5], wherein the oxidation is performed at 85 to 180° C.

[7] The aldehyde production method according to any one of [1] to [6], wherein the poor solvent is a mixture of water and an alcohol.

[8] The aldehyde production method according to any one of [1] to [7], wherein the oxidation and the crystallization are performed under neutral to acidic conditions.

[9] The aldehyde production method according to any one of [1] to [8], wherein the complex catalyst recovered in the above step (2) is fed to the hydroformylation reaction zone.

[10] The aldehyde production method according to any one of [1] to [9], wherein the Group 8 to 10 metal is rhodium.

[11] The aldehyde production method according to any one of [1] to [10], wherein the oxidation is performed for 1 to 5 hours.

[12] A method for producing an alcohol, containing using an aldehyde produced by the method according to any one of [1] to [11].

[13] A method for producing an alcohol, containing producing an aldehyde by the method according to any one of [1] to [11], followed by producing an alcohol from the aldehyde.

[14] An aldehyde production method for producing an aldehyde by a hydroformylation reaction of reacting an olefin with hydrogen and carbon monoxide in the presence of a Group 8 to 10 meal-phosphine complex catalyst, including the following steps (X) and (Y):

(X) a step of withdrawing a reaction solution having accumulated therein a high-boiling-point byproduct from a reaction zone, and oxidizing by subjecting the withdrawn reaction solution to the following (a) and (b):

(a) converting an alkyl-substituted phosphine in the reaction solution to an alkyl-substituted phosphine oxide; and (b) decomposing a cluster complex in the reaction solution, and (Y) a step of, after the step (X), mixing a poor solvent and hydrogen with the reaction solution, then crystallizing the Group 8 to 10 metal-phosphine complex catalyst by crystallization, and recovering the crystallized complex catalyst from the reaction solution.

Effect of the Invention

According to the present invention, an aldehyde production method capable of recovering a highly active complex catalyst, particularly, an expensive Group 8 to 10 metal in the complex catalyst, at a high ratio can be provided. The method is preferable in view of energy efficiency and superior based on economical aspect and environmental aspect.

MODE FOR CARRYING OUT THE INVENTION

Figure 1:
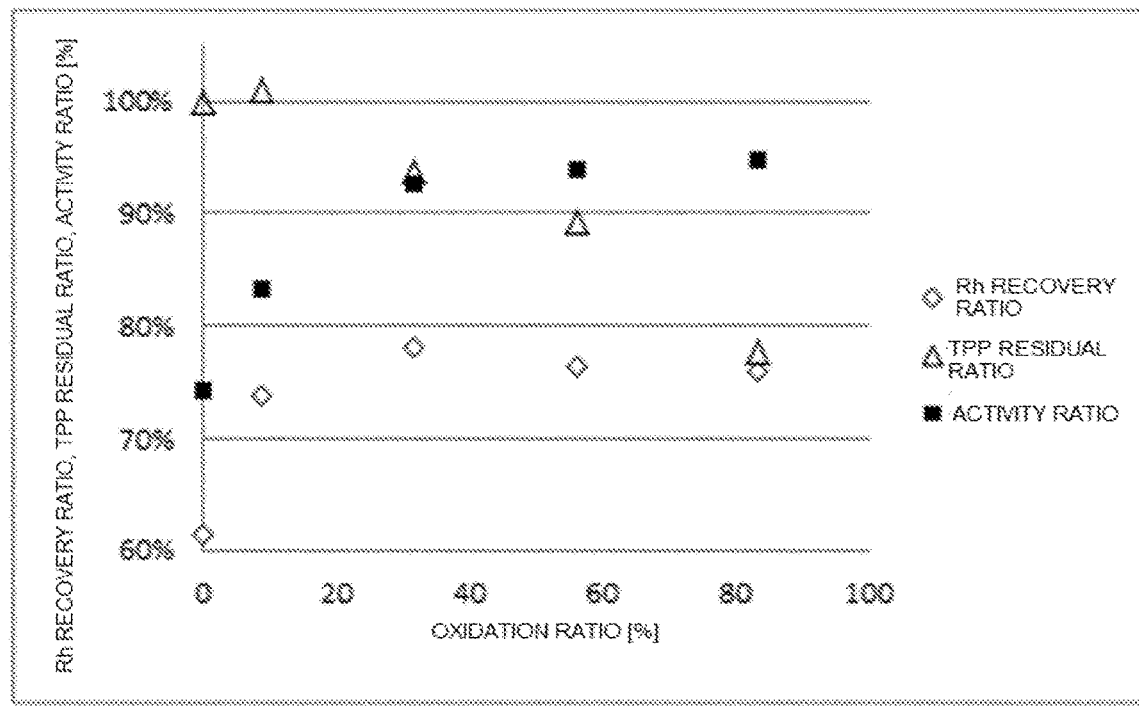
FIG. 1 is a plotted figure which shows relationship among oxidation ratio and recovery ratio of rhodium-phosphine complex catalyst (calculation based on rhodium atom), TPP (triphenyl phosphine) residual ratio and activity ratio of rhodium complex in Examples 1 to 4 and Comparative Example 1.

The present invention is described in detail below.

The first mode of the present invention is a method for producing an aldehyde by a hydroformylation reaction of reacting an olefin with hydrogen and carbon monoxide in the presence of a Group 8 to 10 metal-phosphine complex catalyst, including the following steps (1) and (2):

(1) a step of withdrawing a reaction solution having accumulated therein a high-boiling-point byproduct from a reaction zone and oxidizing by bringing the withdrawn reaction solution into contact with an oxygen-containing gas, and (2) a step of, after the step (1), (2-1) mixing a poor solvent and hydrogen with the reaction solution, (2-2) then crystallizing the Group 8 to 10 metal-phosphine complex catalyst by crystallization, and (2-3) recovering the crystallized complex catalyst from the reaction solution.

Additionally, the second mode of the present invention is a method for producing an aldehyde by a hydroformylation reaction of reacting an olefin with hydrogen and carbon monoxide in the presence of a Group 8 to 10 metal-phosphine complex catalyst, including the following steps (X) and (Y):

(X) a step of withdrawing a reaction solution having accumulated therein a high-boiling-point byproduct from a reaction zone and oxidizing by carrying out the following steps (a) and (b) out for the withdrawn reaction solution:

(a) alkyl-substituted phosphine in the reaction solution is converted to alkyl-substituted phosphine oxide; and (b) a cluster complex in the reaction solution is decomposed, and (Y) a of, after the step (X), (Y-1) mixing a poor solvent and hydrogen with the reaction solution, (Y-2) then crystallizing the Group 8 to 10 metal-phosphine complex catalyst by crystallization, and (Y-3) recovering the crystallized complex catalyst from the reaction solution.

In the present invention, the Group 8 to 10 metal is a metal belongs to a Groups 8 to 10 metal in the long form of the periodic table. Among others, ruthenium, cobalt, rhodium, palladium, and platinum are preferred since they have high activity in case of use as a catalyst, and in particular, rhodium is preferably used since it has high activity.

The phosphine may be sufficient if it is a phosphine having an ability as a monodentate ligand or a multidentate ligand, and includes, for example, a triarylphosphine and a triarylphosphine having, on the phenyl group, a substituent which is inert under the hydroformylation reaction conditions. Specifically, the phosphine includes triphenylphosphine; a phosphine having an alkyl group-substituted phenyl group, such as tris(p-tolyl)phosphine, trixylylphosphine and tris(p-ethylphenyl)phosphine; a phosphine having an alkoxy group-substituted phenyl group, such as tris(p-methoxyphenyl)phosphine; etc., and among others, triphenylphosphine is preferred since it is chemically stable based on low activity and it is easily available.

The Group 8 to 10 metal-phosphine complex catalyst can be prepared by a known complexation reaction from a Group 8 to 10 metal compound and a phosphine. In addition, a Group 8 to 10 metal compound and a phosphine may be fed to a hydroformylation reaction zone to form a Group 8 to 10 metal-phosphine complex in the reaction zone. In this case, the phosphine may be directly introduced into the reaction zone but, considering ease of handling, etc., is preferably introduced after dissolving it in a reaction medium (the solvent used when performing the hydroformylation reaction).

The Group 8 to 10 metal compound includes, for example, a water-soluble inorganic salt or inorganic complex compound such as rhodium chloride, palladium chloride, ruthenium chloride, platinum chloride, rhodium bromide, rhodium iodide, rhodium sulfate, rhodium nitrate, palladium nitrate, rhodium ammonium chloride and sodium rhodium chloride; and a water-soluble organic acid salt such as rhodium formate, rhodium acetate, palladium acetate, rhodium propionate, palladium propionate and rhodium octanoate. In addition, respective metal complex species may also be used. Among these, in view of reaction activity and catalyst cost, rhodium acetate is preferably used.

The hydroformylation reaction is performed by reacting an olefin with hydrogen and carbon monoxide in the presence of a Group 8 to 10 metal-phosphine complex catalyst. Although a carbon number of olefin is not particularly limited, examples thereof include a carbon number of 2 to 20. The olefin having a carbon number of 2 to 20 may be, for example, an α-olefin such as ethylene, propylene, 1-butene, 1-pentene, 1-hexene and 1-octene, or an internal olefin such as 2-butene, 2-pentene, 3-hexene and 4-octene.

As for the reaction medium of the hydroformylation reaction, a medium allowing the dissolution of raw materials and the Group 8 to 10 metal-phosphine complex catalyst, having a higher boiling point than the aldehyde produced, and being free of reaction inhibitory effect is preferred. Examples thereof include an aromatic hydrocarbon such as benzene, toluene and xylene, an aliphatic hydrocarbon such as hexane and octane, esters such as butyl acetate and butyl butyrate ester, and ketones. The concentration of the Group 8 to 10 metal-phosphine complex catalyst in the reaction medium is, in terms of the Group 8 to 10 metal atom, usually from 1 ppm by weight to 10 wt %, and the phosphine used as a ligand is usually caused to be present in an excess amount in the reaction medium so as to, for example, increase the stability of the complex catalyst.

The hydroformylation reaction may be performed under known conditions. For example, in the case of using a rhodium-phosphine complex catalyst, the conditions are appropriately selected in the ranges of a hydrogen partial pressure of 0.01 to 20 MPaG, a carbon monoxide partial pressure of 0.01 to 20 MPaG, a total pressure of 0.02 to 30 MPaG, hydrogen partial pressure/carbon monoxide partial pressure of 0.1 to 10, a reaction temperature of 60 to 200° C., an Rh (rhodium) concentration of several ppm by weight to several wt %, P (free organic phosphorus ligand)/Rh of 2 to 10,000 (molar ratio), and a reaction time of several minutes to a dozen hours.

In the hydroformylation reaction, an aldehyde having a carbon number of n+1 can be obtained from a raw material olefin having a carbon number of n (n is, for example, an integer of 2 to 20). Such an aldehyde includes propionaldehyde, butylaldehyde, pentylaldehyde, hexylaldehyde, heptylaldehyde, octylaldehyde, nonylaldehyde, decylaldehyde, etc. Usually, the aldehyde is obtained as a mixture of a linear form and a branched form.

The hydroformylation reaction is performed under the above-described reaction conditions by using usually a flow-type reactor, but a batch-type reactor may also be used.

The main flow reaction (which uses the above flow-type reactor) system includes a stripping system and a liquid circulating system.

The stripping system is a method in which a reaction solution containing a catalyst is held in a reactor, an olefin and an oxo gas are continuously fed, and the aldehyde produced by the reaction is vaporized within the reactor and taken out of the system.

On the other hand, the liquid circulating system is a method in which an olefin, an oxo gas and a reaction medium containing a catalyst are continuously fed to a reactor and a reaction solution containing the produced aldehyde, the catalyst, the reaction medium, etc. is continuously withdrawn outside the reactor. The reaction solution withdrawn from the reactor is separated into the produced aldehyde and a catalyst-containing reaction solution, for example, by a separation operation such as stripping with an unreacted gas or distillation. The produced aldehyde obtained is withdrawn outside the system, and the catalyst-containing reaction solution is returned to the reactor and is recycled.

In the case of the stripping system, a byproduct of hydroformylation reaction which is a high-boiling-point byproduct accumulates in the catalyst-containing reaction solution held within the reactor and therefore, usually, part of the reaction solution containing the catalyst is intermittently withdrawn outside the reaction zone. In the case of the liquid circulating system, when recycling of the catalyst-containing reaction solution is continued, a byproduct which is a high-boiling-point byproduct accumulates in the reaction zone and therefore, part of the catalyst-containing reaction solution is continuously or intermittently withdrawn outside the reaction zone.

In this connection, the amount of the reaction solution withdrawn may be appropriately determined according to the amount of the high-boiling-point byproduct produced.

In addition, usually, when the reaction solution is withdrawn outside the reaction zone, a catalyst and a phosphine in amounts corresponding to the catalyst and phosphine contained in the withdrawn reaction solution are newly fed to the reaction zone.

The above high boiling point byproduct of hydroformylation reaction is aldehyde condensate etc. which is generated by condensation of aldehyde which is object product by hydroformylation reaction.

In the reaction solution having accumulated therein the high-boiling-point byproduct, a phosphine and a phosphine which is alkyl-substituted (hereinafter, a phosphine which is alkyl-substituted is to be referred to as "an alkyl-substituted phosphine") are present. Additionally, when rhodium is used as Group 8 to 10 metal for example, in the reaction solution wherein the high-boiling-point byproduct accumulates, there are present a rhodium complex, such as:

a complex in which phosphine is coordinated to rhodium (for example, $RhH(PPh_3)_4$ which is a complex in which triphenylphosphine ($PPh_3$) is coordinated to rhodium (Rh));

a complex in which carbon monoxide and phosphine are coordinated to rhodium (for example, $RhH(CO)(PPh_3)_3$);

a complex in which carbon monoxide and an alkyl-substituted phosphine are coordinated to rhodium (for example, $RhH(CO)(PPh_3)(PPh_2R)_2$ or $RhH(CO)(PPh_2R)_3$, wherein R represents an alkyl group), etc.;

a rhodium cluster complex in which a plurality of rhodiums are connected and carbon monoxide and phosphine are coordinated thereto; and a rhodium cluster complex in which an alkyl-substituted phosphine is coordinated to the rhodium cluster complex above.

Among these, a complex in which an alkyl-substituted phosphine is coordinated to rhodium and a rhodium cluster complex exhibit low activity as a complex catalyst. Furthermore, a complex (including a cluster complex), in which an alkyl-substituted phosphine is coordinated, have high solubility in a poor solvent and are less likely to crystallize, in comparison with a complex in which an alkyl-substituted phosphine is not coordinated. Additionally, a complex in which an alkyl-substituted phosphine is not coordinated and at least hydrogen and phosphine are coordinated has high activity and preferably functions as a complex catalyst as a hydroformylation reaction.

Although rhodium is used as an example in the above, the same can be said for other Group 8 to 10 metals.

In the first embodiment of the present invention, it is preferable that the reaction solution having accumulated therein a high-boiling-point byproduct such as aldehyde condensation byproduct is oxidized by being made into contact with gas containing oxygen, and the alkyl-substituted phosphine is thereby oxidized and converted to corresponding alkyl-substituted phosphine oxide. By the conversion, production of an alkyl-substituted phosphine-coordinated complex is suppressed and decrease in reaction activity as complex catalyst and decrease in recovery ratio of Group 8 to 10 metal-phosphine complex can be prevented.

An alkyl-substituted phosphine has higher compatibility for Group 8 to 10 metal in comparison with phosphine and tends to be oxidized.

In addition, in the first embodiment of the present invention, it is preferable that the oxidation leads to decomposition of a complex in which an alkyl-substituted phosphine is coordinated or a cluster complex. Furthermore, a complex obtained by this decomposition can be recovered as a highly active complex catalyst, by performing crystallization with the later-described poor solvent and hydrogen.

In this connection, when rhodium is used as Group 8 to 10 metal, examples of a highly active complex catalyst include $RhH(CO)(PPh_3)_3$ or $RhH(PPh_3)_4$.

The oxidation ratio (%) of an alkyl-substitute phosphine, is preferably from 5 to 80%, more preferably from 10 to 70%, and most preferably from 30 to 60%.

If the oxidation ratio is higher than lower limit of the above ratio range, it is preferable since the amount of an alkyl-substituted phosphine-coordinated complex in a reaction solution decreases; and the recovery ratio of Groups 8 to 10 metals increases. Additionally, if the oxidation ratio is lower than the higher limit of the above ratio range, oxidation of phosphine is suppressed and the amount of phosphine reused in the reaction zone does not decrease, which is preferable.

In this connection, oxidation ratio (%) of an alkyl-substitute phosphine is represented by {(amount of alkyl-substituted phosphine in reaction solution before oxidation− amount of alkyl-substituted phosphine in reaction solution after oxidation)/amount of alkyl-substituted phosphine in reaction solution before oxidation}×100

The change in the amount of an alkyl-substituted phosphine, etc. between before and after oxidation can be detected by a conventional analysis method such as gas chromatography.

In the step (1) in the first embodiment in the present invention is performed by withdrawing the reaction solution from the reaction zone, followed by bringing the reaction solution into contact with an oxygen-containing gas to oxidize. Preferable examples of the oxygen-containing gas include oxygen, air, and a gas obtained by adding an inert gas such as nitrogen to air.

Oxidation in the first embodiment in the present invention is preferably performed at a temperature of 85 to 180° C., more preferably from 90 to 180° C., further more preferably from 110 to 180° C., particularly preferably from 110 to 160° C., and most preferably from 110 to 150° C.

If the temperature is higher than the lower limit of the above range, it is preferable since conversion of the alkyl-substituted phosphine to its corresponding oxide is sufficient, and recovery ratio of Group 8 to 10 metal-phosphine complex catalyst is further higher. If the temperature is lower than the upper limit of the above range, oxidation of phosphine is suppressed, and the amount of phosphine reused in the reaction zone does not decrease, which is preferable.

When the oxidation temperature is from 110 to 150° C., decomposition of the cluster complex is more promoted and the highly active Group 8 to 10 metal complex such as rhodium complex is increased.

The oxidation time in the first embodiment in the present invention varies depending on other conditions such as temperature but, usually, is approximately from several minutes to several hours and 1 to 5 hours is preferable.

In the present invention, after the oxidation, a poor solvent and hydrogen are mixed with the reaction solution, a Group 8 to 10 metal-phosphine complex catalyst such as $RhH(CO)(PPh_3)_3$ or $RhH(PPh_3)_4$ is then crystallized, and the crystallized complex catalyst is recovered from the reaction solution.

The poor solvent indicates a solvent in which the Group 8 to 10 metal compound has smaller solubility than in the reaction solution, and is preferably a solvent that keeps a homogeneous phase with the reaction solution and does not participate in the reaction in the reaction zone. Specifically, the poor solvent includes methanol, ethanol, (n-, i-) propanol, (n-, i-, t-) butanol, acetone, and a mixture thereof with water. In view of the recovery ratio of the Group 8 to 10 metal-phosphine complex catalyst, a mixture of water and an alcohol having a carbon number of 1 to 3 is preferred. As the mixing ratio (volume ratio), the water:alcohol is preferably from 5:1 to 1:5, and more preferably from 1:1 to 1:4. If the ratio of water is higher than the lower limit, the recovery ratio is high for the reason of complex solubility. Additionally, if the ratio of water is lower than the upper limit, the reaction solution tends to be uniform phase, and a good recovery ratio tends to be obtained.

In addition, although the weight ratio of the poor solvent and the reaction solution is determined based on the kind of the poor solvent and the composition of the reaction solution, the poor solvent:reaction solution is, preferably, approximately from 10:1 to 1:2, and further preferably from 5:1 to 1:1. As the ratio of the poor solvent is lower, the size of the crystallization recovery apparatus can be reduced, but in order to obtain a sufficient recovery ratio, it is preferable that the amount of the poor solvent is large.

The reaction solution after oxidation may be directly mixed with the poor solvent and hydrogen or may be mixed with the poor solvent and hydrogen after removing at least part of the reaction medium by distillation, etc.

By mixing a poor solvent and hydrogen with the reaction solution, the Group 8 to 10 metal-phosphine complex catalyst can be changed into a crystallizable form.

The method for mixing a poor solvent and hydrogen with the reaction solution includes, for example, a method of first mixing the reaction solution with a poor solvent and brining the obtained mixed solution into contact with a hydrogen gas, and a method of mixing the reaction solution with a poor solvent in a hydrogen atmosphere. In this case, the hydrogen partial pressure is usually from 0.1 to 10 MPaG, and the contact time with a hydrogen gas is usually from several minutes to several hours. The temperature at the time of contact with hydrogen is usually from 0 to 95° C., preferably from 10 to 30° C.

After mixing a poor solvent and hydrogen with the reaction solution, the Group 8 to 10 metal-phosphine complex catalyst is crystallized by keeping the temperature of the reaction solution at preferably from 0 to 95° C. If the crystallization temperature is too high or too low, the catalyst recovery ratio is insufficient. The pressure at the time of performing the crystallization operation is usually from normal pressure to 10 MPaG. The crystallization time is usually from several minutes to several hours.

The crystallized Group 8 to 10 metal-phosphine complex catalyst is separated and recovered from the liquid by a solid-liquid separation method usually employed. Specifically, the method includes decantation, centrifugal separation, filtration, etc., and in industry, centrifugal filtration is often used. The separation and recovery of the complex catalyst is also preferably performed by keeping the temperature of the mixed solution (reaction solution) at 0 to 95° C.

In the present invention, the reaction solution is oxidized and then subjected to crystallization, and the crystallization time is thereby shortened, compared with the case of performing crystallization without oxidizing the reaction solution, which causes increase in recovery ratio and activity ratio of the Group 8 to 10 metal-phosphine complex catalyst.

In the present invention, the oxidation and the crystallization are performed preferably under neutral to acidic conditions since washing and neutralization operation are not necessary before reuse by returning the catalyst complex to reaction zone It is preferable that the recovered Group 8 to 10 metal-phosphine complex catalyst is dissolved in a reaction medium and fed to the hydroformylation reaction zone.

The activity ratio of the recovered Group 8 to 10 metal-phosphine complex catalyst can be determined by comparing the hydroformylation reaction rate A in a hydroformylation reaction performed using the complex catalyst, and the reaction rate B of the same hydroformylation reaction performed using a new Group 8 to 10 metal-phosphine complex catalyst in the same manner.

Specifically, the activity ratio (%) is represented by the following formula: Activity Ratio (%)=(reaction rate A/reaction rate B)×100.

The above activity ratio can also be determined by comparing the reaction rate of the complex catalyst between immediately before processing the reaction solution according to the oxidation and crystallization of the present invention and immediately after the processing. In this connection, reaction rate can be observed, for example, as a decrease rate of the raw material olefin, carbon monoxide or hydrogen.

In the production method of alcohol in the present invention, aldehydes which are produced by the production method of aldehyde in the present invention is used.

Alcohol can be produce by directly reacting aldehydes with hydrogen, namely hydrogenation reaction, or bringing into hydrogenation reaction after dimerization. In the hydrogenation reaction, known solid catalysts wherein metals such as nickel, chrome and copper are supported in a carrier can be used. Reaction condition thereof is usually temperature of from 60 to 200° C. and hydrogen pressure of from 0.1 to 20 MPag.

EXAMPLES

Although the present invention is described in greater detail below by referring to Examples, the present invention is not limited to the following Examples as long as its gist is observed. In this connection, Oxidation Ratio (%), Rh-Phosphine Complex CatalystRecovery Ratio (%) (calculation based on rhodium atom), TPP (triphenylphosphine) Residual Ratio (%) and Activity Ratio (%) are values calculated by the following formulae.

Oxidation Ratio (%)={(amount of alkyl-substituted phosphine in reaction solution before oxidation–amount of alkyl-substituted phosphine in reaction solution after oxidation)/amount of alkyl-substituted phosphine in reaction solution before oxidation}×100

Rh-Phosphine Complex Catalyst Recovery Ratio (%) (calculation based on rhodium atom)=(amount of Rh in crystallized product after crystallization/amount of Rh contained in reaction solution before crystallization)×100

TPP Residual Ratio (%)=(amount of triphenylphosphine in reaction solution after oxidation/amount of triphenylphosphine in reaction solution before oxidation)×100

Activity Ratio (%)=(reaction rate when hydroformylation reaction is performed using the recovered Rh-phosphine complex catalyst/reaction rate when hydroformylation reaction is performed under the same conditions by using new Rh-phosphine complex catalyst)×100

Example 1

(Recovery of Group 8 to 10 Metal-Phosphine Complex Catalyst)

A hydroformylation reaction of propylene was performed using rhodium acetate as the Group 8 to 10 metal compound and triphenylphosphine as the phosphine ligand. After the completion of reaction, the reaction solution was withdrawn. Next, the reaction solvent was removed by distillation from the reaction solution to obtain a liquid distillation residue having the following composition.

In this connection, the liquid distillation residue was black and transparent.

n-Propyldiphenylphosphine: 1.18 (wt %)
n-Propyldiphenylphosphine oxide: 0.52 (wt %)
Triphenylphosphine: 26.53 (wt %)
Triphenylphosphine oxide: 1.31 (wt %)
Others (various complexes, high-boiling-point byproducts, etc.): 70.46 (wt %)

A stainless steel-made jacketed reactor was charged with 9.96 kg of the liquid distillation residue, and air and nitrogen ($N_2$) were fed at an inner temperature of 150° C. for 0.5 hours at an air feed rate of 1.50 (L/min) and an $N_2$ feed rate of 4.50 (L/min) to perform an oxidation treatment. The liquid distillation residue after the oxidation treatment was analyzed and found to have the following composition, revealing that 9.3 wt % of n-propyldiphenylphosphine was oxidized. In this connection, the liquid distillation residue was amber and transparent. Additionally, TPP Residual Ratio (%) was calculated. A result is described in the Table 1.

n-Propyldiphenylphosphine: 1.07 (wt %)
n-Propyldiphenylphosphine oxide: 0.66 (wt %)
Triphenylphosphine: 26.82 (wt %)
Triphenylphosphine oxide: 2.02 (wt %)
Others (various complexes, high-boiling-point byproducts, etc.): 69.43 (wt %)

Subsequently, 80 g of the liquid distillation residue after the oxidation treatment and 331 g of a mixed solvent of isopropyl alcohol and water (isopropyl alcohol:water=65:35 (weight ratio)) were put in an autoclave of an electromagnetic induction stirrer having a volume of 0.5 L in an inert gas atmosphere. After tightly closing the autoclave, a hydrogen gas was injected at a temperature of 15° C. to reach a pressure of 0.9 MPaG while stirring the contents at 611 rpm, and the system was held at the pressure and temperature above for 2 hours to precipitate a rhodium complex. Thereafter, the hydrogen gas was purged, and solid-liquid separation was performed by normal vacuum filtration. The amount of the separated rhodium complex was quantified, and the recovery ratio of rhodium complex was determined. As a result, the recovery ratio was 73.8 wt % in terms of rhodium atom.

(Production of Aldehyde)

The recovered rhodium complex, triphenylphosphine and toluene were mixed to have the following concentrations and after 150 ml of the resulting mixed solution was put in a vertical agitation-type autoclave having a volume of 0.5 L in a nitrogen atmosphere, the autoclave was tightly closed.

Rhodium complex (in terms of rhodium atom): 276 (mg/L)
Triphenylphosphine: 12.40 (wt %)
Toluene: 87.50 (wt %)

After that, 10 g of propylene was put in the autoclave, and the temperature was raised to 110° C. A mixed gas of hydrogen and carbon monoxide (hydrogen:carbon monoxide=1:1 (weight ratio)) was then injected such that the pressure of the gas becomes 5.0 MPaG, and a hydroformylation reaction was performed for 1.5 hours while maintaining the pressure and temperature above. The reaction rate of the hydroformylation reaction was calculated from the ratio of decrease in carbon monoxide during the hydroformylation reaction, and the rhodium complex activity ratio (activity ratio) was determined. The obtained activity ratio was 83.2%.

Example 2

(Recovery of Group 8 to 10 Metal-Phosphine Complex Catalyst)

A hydroformylation reaction of propylene was performed using rhodium acetate as the Group 8 to 10 metal compound and triphenylphosphine as the phosphine ligand. After the completion of reaction, the reaction solution was withdrawn. Next, the reaction solvent was removed by distillation from the reaction solution to obtain a liquid distillation residue having the following composition.

In this connection, the liquid distillation residue was black and transparent.

n-Propyldiphenylphosphine: 1.19 (wt %)
n-Propyldiphenylphosphine oxide: 0.62 (wt %)
Triphenylphosphine: 25.81 (wt %)
Triphenylphosphine oxide: 1.78 (wt %)
Others (various complexes, high-boiling-point byproducts, etc.): 70.60 (wt %)

A stainless steel-made jacketed reactor was charged with 471 g of the liquid distillation residue, and air and nitrogen ($N_2$) were fed at an inner temperature of 150° C. for 1 hour at an air feed rate of 0.50 (L/min) and an $N_2$ feed rate of 1.51 (L/min) to perform an oxidation treatment. The liquid distillation residue after the oxidation treatment was analyzed and found to have the following composition, revealing that 31.1 wt % of n-propyldiphenylphosphine was oxidized. In this connection, the liquid distillation residue was transparent amber in color and thus, it was confirmed that the cluster complex was decomposed. Additionally, TPP Residual Ratio (%) was calculated. A result is described in the Table 1.

n-Propyldiphenylphosphine: 0.82 (wt %)
n-Propyldiphenylphosphine oxide: 0.99 (wt %)
Triphenylphosphine: 24.18 (wt %)
Triphenylphosphine oxide: 3.13 (wt %)
Others (various complexes, high-boiling-point byproducts, etc.): 70.88 (wt %)

Subsequently, 80 g of the liquid distillation residue after the oxidation treatment and 330 g of a mixed solvent of isopropyl alcohol and water (isopropyl alcohol:water=65:35 (weight ratio)) were put in an autoclave of an electromagnetic induction stirrer having a volume of 0.5 L in an inert gas atmosphere. After tightly closing the autoclave, a hydrogen gas was injected at a temperature of 15° C. to reach a pressure of 0.9 MPaG while stirring the contents at 611 rpm, and the system was held at the pressure and temperature above for 2 hours to precipitate a rhodium complex. Thereafter, the hydrogen gas was purged, and solid-liquid separation was performed by normal vacuum filtration. The amount of the separated rhodium complex was quantified, and the recovery ratio of rhodium complex was determined, as a result, the recovery ratio was 78.2 wt % in terms of rhodium atom.

(Production of Aldehyde)

The recovered rhodium complex, triphenylphosphine and toluene were mixed to have the following concentrations and after 150 ml of the resulting mixed solution was put in a vertical agitation-type autoclave having a volume of 0.5 L in a nitrogen atmosphere, the autoclave was tightly closed.

Rhodium complex (in terms of rhodium atom): 292 (mg/L)
Triphenylphosphine: 13.01 (wt %)
Toluene: 86.98 (wt %)

After that, 10 g of propylene was put in the autoclave, and the temperature was raised to 110° C. A mixed gas of hydrogen and carbon monoxide (hydrogen:carbon monoxide=1:1 (weight ratio)) was then injected such that the pressure of the gas becomes 5.0 MPaG, and a hydroformylation reaction was performed for 1.5 hours while maintaining the pressure and temperature above. The activity ratio of the hydroformylation reaction was calculated from the ratio of decrease in carbon monoxide during the hydroformylation reaction, and the rhodium complex activity ratio (activity ratio) was determined. The obtained activity ratio was 92.7%.

Example 3

(Recovery of Group 8 to 10 Metal-Phosphine Complex Catalyst)

A hydroformylation reaction of propylene was performed using rhodium acetate as the Group 8 to 10 metal compound and triphenylphosphine as the phosphine ligand. After the completion of reaction, the reaction solution was withdrawn. Next, the reaction solvent was removed by distillation from the reaction solution to obtain a liquid distillation residue having the following composition.

In this connection, the liquid distillation residue was black and transparent.

n-Propyldiphenylphosphine: 1.16 (wt %)
n-Propyldiphenylphosphine oxide: 0.68 (wt %)
Triphenylphosphine: 25.70 (wt %)
Triphenylphosphine oxide: 1.87 (wt %)
Others (various complexes, high-boiling-point byproducts, etc.): 70.59 (wt %)

A stainless steel-made jacketed reactor was charged with 454 g of the liquid distillation residue, and air and nitrogen ($N_2$) were fed at an inner temperature of 150° C. for 2 hours at an air feed rate of 0.50 (L/min) and an $N_2$ feed rate of 1.51 (L/min) to perform an oxidation treatment. The liquid distillation residue after the oxidation treatment was analyzed and found to have the following composition, revealing that 56.0 wt % of n-propyldiphenylphosphine was oxidized. In this connection, the liquid distillation residue was transparent amber in color and thus, it was confirmed that the cluster complex was decomposed. Additionally, TPP Residual Ratio (%) was calculated. A result is described in the Table 1.
  n-Propyldiphenylphosphine: 0.51 (wt %)
  n-Propyldiphenylphosphine oxide: 1.28 (wt %)
  Triphenylphosphine: 22.94 (wt %)
  Triphenylphosphine oxide: 4.56 (wt %)
  Others (various complexes, high-boiling-point byproducts, etc.): 70.71 (wt %)

Subsequently, 80 g of the liquid distillation residue after the oxidation treatment and 330 g of a mixed solvent of isopropyl alcohol and water (isopropyl alcohol:water=65:35 (weight ratio)) were put in an autoclave of an electromagnetic induction stirrer having a volume of 0.5 L in an inert gas atmosphere. After tightly closing the autoclave, a hydrogen gas was injected at a temperature of 15° C. to reach a pressure of 0.9 MPaG while stirring the contents at 611 rpm, and the system was held at the pressure and temperature above for 2 hours to precipitate a rhodium complex. Thereafter, the hydrogen gas was purged, and solid-liquid separation was performed by normal vacuum filtration. The amount of the separated rhodium complex was quantified, and the recovery ratio of rhodium complex was determined, as a result, the recovery ratio was 76.4 wt % in terms of rhodium atom.

(Production of Aldehyde)

The recovered rhodium complex, triphenylphosphine and toluene were mixed to have the following concentrations and after 150 ml of the resulting mixed solution was put in a vertical agitation-type autoclave having a volume of 0.5 L in a nitrogen atmosphere, the autoclave was tightly closed.
  Rhodium complex (in terms of rhodium atom): 248 (mg/L)
  Triphenylphosphine: 12.45 (wt %)
  Toluene: 87.54 (wt %)

After that, 10 g of propylene was put in the autoclave, and the temperature was raised to 110° C. A mixed gas of hydrogen and carbon monoxide (hydrogen:carbon monoxide=1:1 (weight ratio)) was then injected such that the pressure of the gas becomes 5.0 MPaG, and a hydroformylation reaction was performed for 1.5 hours while maintaining the pressure and temperature above. The reaction rate of the hydroformylation reaction was calculated from the ratio of decrease in carbon monoxide during the hydroformylation reaction, and the rhodium complex activity ratio (activity ratio) was determined. The obtained activity ratio was 93.9%.

Example 4

(Recovery of Group 8 to 10 Metal-Phosphine Complex Catalyst)

A hydroformylation reaction of propylene was performed using rhodium acetate as the Group 8 to 10 metal compound and triphenylphosphine as the phosphine ligand. After the completion of reaction, the reaction solution was withdrawn. Next, the reaction solvent was removed by distillation from the reaction solution to obtain a liquid distillation residue having the following composition.

In this connection, the liquid distillation residue was black and transparent.
  n-Propyldiphenylphosphine: 1.20 (wt %)
  n-Propyldiphenylphosphine oxide: 0.67 (wt %)
  Triphenylphosphine: 25.98 (wt %)
  Triphenylphosphine oxide: 1.80 (wt %)
  Others (various complexes, high-boiling-point byproducts, etc.): 70.35 (wt %)

A stainless steel-made jacketed reactor was charged with 462 g of the liquid distillation residue, and air and nitrogen ($N_2$) were fed at an inner temperature of 150° C. for 4 hours at an air feed rate of 0.5 (L/min) and an $N_2$ feed rate of 1.5 (L/min) to perform an oxidation treatment. The liquid distillation residue after the oxidation treatment was analyzed and found to have the following composition, revealing that 83.3 wt % of n-propyldiphenylphosphine was oxidized. In this connection, the liquid distillation residue was transparent amber in color and thus, it was confirmed that the cluster complex was decomposed. Additionally, TPP Residual Ratio (%) was calculated. A result is described in the Table 1.
  n-Propyldiphenylphosphine: 0.20 (wt %)
  n-Propyldiphenylphosphine oxide: 1.58 (wt %)
  Triphenylphosphine: 20.16 (wt %)
  Triphenylphosphine oxide: 6.89 (wt %)
  Others (various complexes, high-boiling-point byproducts, etc.): 71.17 (wt %)

Subsequently, 80 g of the liquid distillation residue after the oxidation treatment and 330 g of a mixed solvent of isopropyl alcohol and water (isopropyl alcohol:water=65:35 (weight ratio)) were put in an autoclave of an electromagnetic induction stirrer having a volume of 0.5 L in an inert gas atmosphere. After tightly closing the autoclave, a hydrogen gas was injected at a temperature of 15° C. to reach a pressure of 0.9 MPaG while stirring the contents at 611 rpm, and the system was held at the pressure and temperature above for 2 hours to precipitate a rhodium complex. Thereafter, the hydrogen gas was purged, and solid-liquid separation was performed by normal vacuum filtration. The amount of the separated rhodium complex was quantified, and the recovery ratio of rhodium complex was determined. As a result, the recovery ratio was 76.0 wt % in terms of rhodium atom.

(Production of Aldehyde)

The recovered rhodium complex, triphenylphosphine and toluene were mixed to have following concentrations and after 150 ml of the resulting mixed solution was put in a vertical agitation-type autoclave having a volume of 0.5 L in a nitrogen atmosphere, the autoclave was tightly closed.
  Rhodium complex (in terms of rhodium atom): 293 (mg/L)
  Triphenylphosphine: 12.39 (wt %)
  Toluene: 87.60 (wt %)

After that, 10 g of propylene was put in the autoclave, and the temperature was raised to 110° C. A mixed gas of hydrogen and carbon monoxide (hydrogen:carbon monoxide=1:1 (weight ratio)) was then injected such that the pressure of the gas becomes 5.0 MPaG, and a hydroformylation reaction was performed for 1.5 hours while maintaining the pressure and temperature above. The reaction rate of the hydroformylation reaction was calculated from the ratio of decrease in carbon monoxide during the hydroformylation reaction, and the rhodium complex activity ratio (activity ratio) was determined. The obtained activity ratio was 94.8%.

Example 5

(Recovery of Group 8 to 10 Metal-Phosphine Complex Catalyst)

A hydroformylation reaction of propylene was performed using rhodium acetate as the Group 8 to 10 metal compound and triphenylphosphine as the phosphine ligand. After the completion of reaction, the reaction solution was withdrawn. Next, the reaction solvent was removed by distillation from the reaction solution to obtain a liquid distillation residue having the following composition.

In this connection, the liquid distillation residue was black and transparent.

n-Propyldiphenylphosphine: 1.29 (wt %)
n-Propyldiphenylphosphine oxide: 0.55 (wt %)
Triphenylphosphine: 26.33 (wt %)
Triphenylphosphine oxide: 1.43 (wt %)
Others (various complexes, high-boiling-point byproducts, etc.): 70.40 (wt %)

A stainless steel-made jacketed reactor was charged with 10.1 kg of the liquid distillation residue, and air and nitrogen ($N_2$) were fed at an inner temperature of 90° C. for 2 hours at an air feed rate of 1.50 (L/min) and an $N_2$ feed rate of 4.50 (L/min) to perform an oxidation treatment. The liquid distillation residue after the oxidation treatment was analyzed and found to have the following composition, revealing that 34.9 wt % of n-propyldiphenylphosphine was oxidized. In this connection, the liquid distillation residue was transparent amber in color and thus, it was confirmed that the cluster complex was decomposed. Additionally, TPP Residual Ratio (%) was calculated. A result is described in the Table 1.

n-Propyldiphenylphosphine: 0.84 (wt %)
n-Propyldiphenylphosphine oxide: 0.92 (wt %)
Triphenylphosphine: 25.93 (wt %)
Triphenylphosphine oxide: 2.49 (wt %)
Others (various complexes, high-boiling-point byproducts, etc.): 69.82 (wt %)

Subsequently, 80 g of the liquid distillation residue after the oxidation treatment and 330 g of a mixed solvent of isopropyl alcohol and water (isopropyl alcohol:water=65:35 (weight ratio)) were put in an autoclave of an electromagnetic induction stirrer having a volume of 0.5 L in an inert gas atmosphere. After tightly closing the autoclave, a hydrogen gas was injected at a temperature of 15° C. to reach a pressure of 0.9 MPaG while stirring the contents at 611 rpm, and the system was held at the pressure and temperature above for 2 hours to precipitate a rhodium complex. Thereafter, the hydrogen gas was purged, and solid-liquid separation was performed by normal vacuum filtration. The amount of the separated rhodium complex was quantified, and the recovery ratio of rhodium complex was determined, as a result, the recovery ratio was 74.6 wt % in terms of rhodium atom.

(Production of Aldehyde)

The recovered rhodium complex, triphenylphosphine and toluene were mixed to have the following concentrations and after 150 ml of the resulting mixed solution was put in a vertical agitation-type autoclave having a volume of 0.5 L in a nitrogen atmosphere, the autoclave was tightly closed.

Rhodium complex (in terms of rhodium atom): 274 (mg/L)
Triphenylphosphine: 12.45 (wt %)
Toluene: 87.54 (wt %)

After that, 10 g of propylene was put in the autoclave, and the temperature was raised to 110° C. A mixed gas of hydrogen and carbon monoxide (hydrogen:carbon monoxide=1:1 (weight ratio)) was then injected such that the pressure of the gas becomes 5.0 MPaG, and a hydroformylation reaction was performed for 1.5 hours while maintaining the pressure and temperature above. The reaction rate of the hydroformylation reaction was calculated from the ratio of decrease in carbon monoxide during the hydroformylation reaction, and the rhodium complex activity ratio (activity ratio) was determined. The obtained activity ratio was 82.2%.

Example 6

(Recovery of Group 8 to 10 Metal-Phosphine Complex Catalyst)

A hydroformylation reaction of propylene was performed using rhodium acetate as the Group 8 to 10 metal compound and triphenylphosphine as the phosphine ligand. After the completion of reaction, the reaction solution was withdrawn. Next, the reaction solvent was removed by distillation from the reaction solution to obtain a liquid distillation residue having the following composition.

In this connection, the liquid distillation residue was black and transparent.

n-Propyldiphenylphosphine: 1.03 (wt %)
n-Propyldiphenylphosphine oxide: 0.51 (wt %)
Triphenylphosphine: 25.15 (wt %)
Triphenylphosphine oxide: 1.63 (wt %)
Others (various complexes, high-boiling-point byproducts, etc.): 71.68 (wt %)

A stainless steel-made jacketed reactor was charged with 498 g of the liquid distillation residue, and air and nitrogen ($N_2$) were fed at an inner temperature of 110° C. for 2 hours at an air feed rate of 0.04 (L/min) and an $N_2$ feed rate of 0.16 (L/min) to perform an oxidation treatment. The liquid distillation residue after the oxidation treatment was analyzed and found to have the following composition, revealing that 63.1 wt % of n-propyldiphenylphosphine was oxidized. In this connection, the liquid distillation residue was transparent amber in color and thus, it was confirmed that the cluster complex was decomposed. Additionally, TPP Residual Ratio (%) was calculated. A result is described in the Table 1.

n-Propyldiphenylphosphine: 0.38 (wt %)
n-Propyldiphenylphosphine oxide: 1.17 (wt %)
Triphenylphosphine: 21.46 (wt %)
Triphenylphosphine oxide: 5.64 (wt %)
Others (various complexes, high-boiling-point byproducts, etc.): 71.35 (wt %)

Subsequently, 80 g of the liquid distillation residue after the oxidation treatment and 330 g of a mixed solvent of isopropyl alcohol and water (isopropyl alcohol:water=65:35 (weight ratio)) were put in an autoclave of an electromagnetic induction stirrer having a volume of 0.5 L in an inert gas atmosphere. After tightly closing the autoclave, a hydrogen gas was injected at a temperature of 15° C. to reach a pressure of 0.9 MPaG while stirring the contents at 611 rpm, and the system was held at the pressure and temperature above for 2 hours to precipitate a rhodium complex. Thereafter, the hydrogen gas was purged, and solid-liquid separation was performed by normal vacuum filtration. The amount of the separated rhodium complex was quantified, and the recovery ratio of rhodium complex was determined, as a result, the recovery ratio was 76.5 wt % in terms of rhodium atom.

(Production of Aldehyde)

The recovered rhodium complex, triphenylphosphine and toluene were mixed to have the following concentrations and after 150 ml of the resulting mixed solution was put in a vertical agitation-type autoclave having a volume of 0.5 L in a nitrogen atmosphere, the autoclave was tightly closed.

Rhodium complex (in terms of rhodium atom): 276 (mg/L)
Triphenylphosphine: 12.20 (wt %)
Toluene: 87.70 (wt %)

After that, 10 g of propylene was put in the autoclave, and the temperature was raised to 110° C. A mixed gas of hydrogen and carbon monoxide (hydrogen:carbon monoxide=1:1 (weight ratio)) was then injected such that the pressure of the gas becomes 5.0 MPaG, and a hydroformylation reaction was performed for 1.5 hours while maintaining the pressure and temperature above. The reaction rate of the hydroformylation reaction was calculated from the ratio of decrease in carbon monoxide during the hydroformylation reaction, and the rhodium complex activity ratio (activity ratio) was determined. The obtained activity ratio was 92.9%.

Example 7

(Recovery of Group 8 to 10 Metal-Phosphine Complex Catalyst)

A hydroformylation reaction of propylene was performed using rhodium acetate as the Group 8 to 10 metal compound and triphenylphosphine as the phosphine ligand. After the completion of reaction, the reaction solution was withdrawn. Next, the reaction solvent was removed by distillation from the reaction solution to obtain a liquid distillation residue having the following composition.

In this connection, the liquid distillation residue was black and transparent.

n-Propyldiphenylphosphine: 1.15 (wt %)
n-Propyldiphenylphosphine oxide: 0.58 (wt %)
Triphenylphosphine: 25.33 (wt %)
Triphenylphosphine oxide: 1.50 (wt %)
Others (various complexes, high-boiling-point byproducts, etc.): 71.44 (wt %)

A stainless steel-made jacketed reactor was charged with 498 g of the liquid distillation residue, and air and nitrogen ($N_2$) were fed at an inner temperature of 150° C. for 2 hours at an air feed rate of 1.51 (L/min) and an $N_2$ feed rate of 4.51 (L/min) to perform an oxidation treatment. The liquid distillation residue after the oxidation treatment was analyzed and found to have the following composition, revealing that 46.1 wt % of n-propyldiphenylphosphine was oxidized. In this connection, the liquid distillation residue was black and transparent. Additionally, TPP Residual Ratio (%) was calculated. A result is described in the Table 1.

n-Propyldiphenylphosphine: 0.62 (wt %)
n-Propyldiphenylphosphine oxide: 1.08 (wt %)
Triphenylphosphine: 22.47 (wt %)
Triphenylphosphine oxide: 3.82 (wt %)
Others (various complexes, high-boiling-point byproducts, etc.): 72.01 (wt %)

Subsequently, 80 g of the liquid distillation residue after the oxidation treatment and 330 g of a mixed solvent of isopropyl alcohol and water (isopropyl alcohol:water=65:35 (weight ratio)) were put in an autoclave of an electromagnetic induction stirrer having a volume of 0.5 L in an inert gas atmosphere. After tightly closing the autoclave, a hydrogen gas was injected at a temperature of 15° C. to reach a pressure of 0.9 MPaG while stirring the contents at 611 rpm, and the system was held at the pressure and temperature above for 2 hours to precipitate a rhodium complex. Thereafter, the hydrogen gas was purged, and solid-liquid separation was performed by normal vacuum filtration. The amount of the separated rhodium complex was quantified, and the recovery ratio of rhodium complex was determined, as a result, the recovery ratio was 82.5 wt % in terms of rhodium atom.

(Production of Aldehyde)

The recovered rhodium complex, triphenylphosphine and toluene were mixed to have the following concentrations and after 150 ml of the resulting mixed solution was put in a vertical agitation-type autoclave having a volume of 0.5 L in a nitrogen atmosphere, the autoclave was tightly closed.

Rhodium complex (in terms of rhodium atom): 225 (mg/L)
Triphenylphosphine: 11.89 (wt %)
Toluene: 88.10 (wt %)

After that, 10 g of propylene was put in the autoclave, and the temperature was raised to 110° C. A mixed gas of hydrogen and carbon monoxide (hydrogen:carbon monoxide=1:1 (weight ratio)) was then injected such that the pressure of the gas becomes 5.0 MPaG, and a hydroformylation reaction was performed for 1.5 hours while maintaining the pressure and temperature above. The reaction rate of the hydroformylation reaction was calculated from the ratio of decrease in carbon monoxide during the hydroformylation reaction, and the rhodium complex activity ratio (activity ratio) was determined. The obtained activity ratio was 98.6%.

Comparative Example 1

(Recovery of Group 8 to 10 Metal-Phosphine Complex Catalyst)

A hydroformylation reaction of propylene was performed using rhodium acetate as the Group 8 to 10 metal compound and triphenylphosphine as the phosphine ligand. After the completion of reaction, the reaction solution was withdrawn. Next, the reaction solvent was removed by distillation from the reaction solution to obtain a liquid distillation residue having the following composition.

In this connection, the liquid distillation residue was black and transparent. Additionally, TPP Residual Ratio (%) was calculated. A result is described in the Table 1.

n-Propyldiphenylphosphine: 1.20 (wt %)
n-Propyldiphenylphosphine oxide: 0.62 (wt %)
Triphenylphosphine: 25.94 (wt %)
Triphenylphosphine oxide: 1.75 (wt %)
Others (various complexes, high-boiling-point byproducts, etc.): 70.49 (wt %)

Subsequently, 80 g of the liquid distillation residue and 330 g of a mixed solvent of isopropyl alcohol and water (isopropyl alcohol:water=65:35 (weight ratio)) were put in an autoclave of an electromagnetic induction stirrer having a volume of 0.5 L in an inert gas atmosphere. After tightly closing the autoclave, a hydrogen gas was injected at a temperature of 15° C. to reach a pressure of 0.9 MPaG while stirring the contents at 611 rpm, and the system was held at the pressure and temperature above for 2 hours to precipitate a rhodium complex. Thereafter, the hydrogen gas was purged, and solid-liquid separation was performed by normal vacuum filtration. The amount of the separated rhodium complex was quantified, and the recovery ratio of rhodium complex was determined, as a result, the recovery ratio was 61.6 wt % in terms of rhodium atom.

(Production of Aldehyde)

The recovered rhodium complex, triphenylphosphine and toluene were mixed to have the following concentrations and after 150 ml of the resulting mixed solution was put in a vertical agitation-type autoclave having a volume of 0.5 L in a nitrogen atmosphere, the autoclave was tightly closed.

Rhodium complex (in terms of rhodium atom): 247 (mg/L)
Triphenylphosphine: 14.50 (wt %)
Toluene: 85.40 (wt %)

After that, 10 g of propylene was put in the autoclave, and the temperature was raised to 110° C. A mixed gas of hydrogen and carbon monoxide (hydrogen:carbon monoxide=1:1 (weight ratio)) was then injected such that the pressure of the gas becomes 5.0 MPaG, and a hydroformylation reaction was performed for 1.5 hours while maintaining the pressure and temperature above. The reaction rate of the hydroformylation reaction was calculated from the ratio of decrease in carbon monoxide during the hydroformylation reaction, and the rhodium complex activity ratio (activity ratio) was determined. The obtained activity ratio was 74.7%.

TABLE 1

| | | Example 1 | | Example 2 | | Example 3 | | Example 4 | |
|---|---|---|---|---|---|---|---|---|---|
| Oxidation conditions | Oxidation temperature (° C.) | 150 | | 150 | | 150 | | 150 | |
| | Oxidation time (hr) | 0.5 | | 1 | | 2 | | 4 | |
| | Air feed rate (l/min) | 1.50 | | 0.50 | | 0.50 | | 0.50 | |
| | Nitrogen feed rate (l/min) | 4.50 | | 1.51 | | 1.51 | | 1.50 | |
| Liquid composition | | before oxidation | after oxidation | before oxidation | after oxidation | before oxidation | after oxidation | before oxidation | after oxidation |
| | n-Propyldiphenyl-phosphine (wt %) | 1.18 | 1.07 | 1.19 | 0.82 | 1.16 | 0.51 | 1.20 | 0.20 |
| | n-Propyldiphenyl-phosphine oxide (wt %) | 0.52 | 0.66 | 0.62 | 0.99 | 0.68 | 1.28 | 0.67 | 1.58 |
| | Triphenylphosphine (wt %) | 26.53 | 26.82 | 25.81 | 24.18 | 25.70 | 22.94 | 25.98 | 20.16 |
| | Triphenylphosphine oxide (wt %) | 1.31 | 2.02 | 1.78 | 3.13 | 1.87 | 4.56 | 1.80 | 6.89 |
| | Others (various complexes, high-boiling-point byproducts, etc.) (wt %) | 70.46 | 69.43 | 70.60 | 70.88 | 70.59 | 70.71 | 70.35 | 71.17 |
| Oxidation ratio | n-Propyldiphenyl-phosphine oxidation ratio (%) | 9.3 | | 31.1 | | 56.0 | | 83.3 | |
| Crystallization conditions | Amount of poor solvent (g) | 331 | | 330 | | 330 | | 330 | |
| | Crystallization temperature (° C.) | 15 | | 15 | | 15 | | 15 | |
| | Hydrogen gas partial pressure (MPaG) | 0.9 | | 0.9 | | 0.9 | | 0.9 | |
| | Crystallization time (hr) | 2 | | 2 | | 2 | | 2 | |
| Results | Recovery ratio (wt %, in terms of Rh) | 73.8 | | 78.2 | | 76.4 | | 76.0 | |
| | TPP Residual ratio (wt %) | 101.1 | | 93.7 | | 89.2 | | 77.6 | |
| | Activity ratio (%) | 83.2 | | 92.7 | | 93.9 | | 94.8 | |

| | | Example 5 | | Example 6 | | Example 7 | | Comparative Example 1 | |
|---|---|---|---|---|---|---|---|---|---|
| Oxidation conditions | Oxidation temperature (° C.) | 90 | | 110 | | 150 | | — | |
| | Oxidation time (hr) | 2 | | 2 | | 2 | | — | |
| | Air feed rate (l/min) | 1.50 | | 0.04 | | 1.51 | | — | |
| | Nitrogen feed rate (l/min) | 4.50 | | 0.16 | | 4.51 | | — | |
| Liquid composition | | before oxidation | after oxidation | before oxidation | after oxidation | before oxidation | after oxidation | before oxidation | after oxidation |
| | n-Propyldiphenyl-phosphine (wt %) | 1.29 | 0.84 | 1.03 | 0.38 | 1.15 | 0.62 | 1.20 | — |
| | n-Propyldiphenyl-phosphine oxide (wt %) | 0.55 | 0.92 | 0.51 | 1.17 | 0.58 | 1.08 | 0.62 | — |
| | Triphenylphosphine (wt %) | 26.33 | 25.93 | 25.15 | 21.46 | 25.33 | 22.47 | 25.94 | — |
| | Triphenylphosphine oxide (wt %) | 1.43 | 2.49 | 1.63 | 5.64 | 1.50 | 3.82 | 1.75 | — |
| | Others (various complexes, high-boiling- | 70.40 | 69.82 | 71.68 | 71.35 | 71.44 | 72.01 | 70.49 | — |

TABLE 1-continued

| | | | | | |
|---|---|---|---|---|---|
| Oxidation ratio | point byproducts, etc.) (wt %) n-Propyldiphenyl-phosphine oxidation ratio (%) | 34.9 | 63.1 | 46.1 | 0.0 |
| Crystallization conditions | Amount of poor solvent (g) | 330 | 330 | 330 | 330 |
| | Crystallization temperature (° C.) | 15 | 15 | 15 | 15 |
| | Hydrogen gas partial pressure (MPaG) | 0.9 | 0.9 | 0.9 | 0.9 |
| | Crystallization time (hr) | 2 | 2 | 2 | 2 |
| Results | Recovery ratio (wt %, in terms of Rh) | 74.6 | 76.5 | 82.5 | 61.6 |
| | TPP Residual ratio (wt %) | 98.5 | 85.3 | 88.7 | 100.0 |
| | Activity ratio (%) | 82.2 | 92.9 | 98.6 | 74.7 |

In this connection, in Examples 1 to 4 and Comparative Example 1, relationship among oxidation ratio and recovery ratio of rhodium complex, TPP residual ratio and activity ratio of rhodium complex is shown in FIG. 1.

Examples 8 to 11

Figure 2:
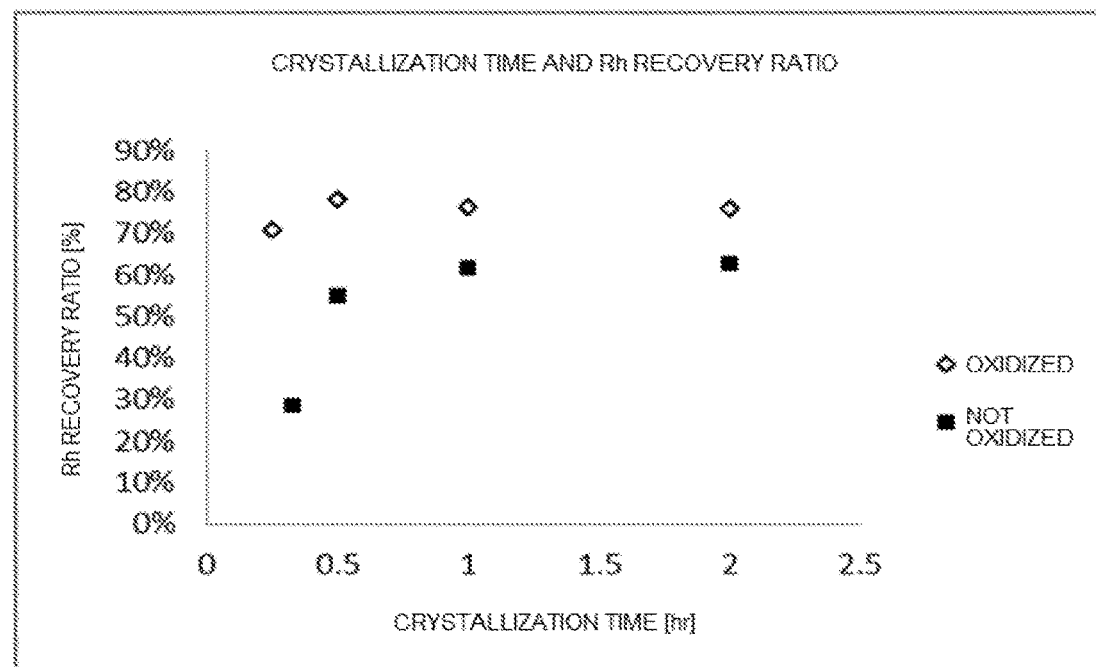
FIG. 2 is a plotted figure which shows relationship between crystallization time and recovery ratio of rhodium-phosphine complex catalyst (calculation based on rhodium atom) in Examples 8 to 11 and Comparative Examples 2 to 5.

In an autoclave of an electromagnetic induction stirrer having a volume of 0.5 L in an inert gas atmosphere, 80 g of the liquid distillation residue after the oxidation treatment of Example 3 and 330 g of a mixed solvent of isopropyl alcohol and water (isopropyl alcohol:water=65:35 (weight ratio)) were put. After tightly closing the autoclave, a hydrogen gas was injected at a temperature of 15° C. to reach a pressure of 0.9 MPaG while stirring the contents at 611 rpm. At the pressure and temperature above, the holding time (crystallization time) was varied to 15 minutes (Example 8), 0.5 hour (Example 9), 1 hour (Example 10) and 2 hours (Example 11). The amount of the precipitated rhodium complex here was quantified in the same manner as in Example 3, and the recovery ratio (in terms of rhodium atom) of rhodium complex was determined. FIG. 2 illustrates the relationship between the crystallization time and the recovery ratio.

Comparative Examples 2 to 5

In an autoclave of an electromagnetic induction stirrer having a volume of 0.5 L in an inert gas atmosphere, 80 g of the liquid distillation residue before the oxidation treatment of Example 3 and 330 g of a mixed solvent of isopropyl alcohol and water (isopropyl alcohol:water=65:35 (weight ratio)) were put. After tightly closing the autoclave, a hydrogen gas was injected at a temperature of 15° C. to reach a pressure of 0.9 MPaG while stirring the contents at 611 rpm. At the pressure and temperature above, the holding time (crystallization time) was varied to 20 minutes (Comparative Example 2), 0.5 hours (Comparative Example 3), 1 hour (Comparative Example 4) and 2 hours (Comparative Example 5). The amount of the precipitated rhodium complex here was quantified in the same manner as in Example 3, and the recovery ratio (in terms of rhodium atom) of rhodium complex was determined. FIG. 2 illustrates the relationship between the crystallization time and the recovery ratio.

As illustrated in FIG. 2, the crystallization time until reaching a maximum recovery ratio is 0.5 hour in the case of performing oxidation of the reaction solution but was 1 hour when the oxidation was not performed. It is understood from these results that by oxidizing the reaction solution, in addition to increase in recovery ratio, the crystallization time is shortened and an Rh-phosphine complex catalyst can be efficiently recovered.

Although the present invention has been explained in detail using specific embodiments, it is obvious to one skilled in the art that various changes and modifications can be made without departing from the intention and the scope of the present invention. The present application is based on a Japanese patent application filed on Nov. 15, 2017 (patent application No. 2017-219776), which is hereby incorporated by reference in its entirety.

The invention claimed is:

1. A method for producing an aldehyde by a hydroformylation reaction of reacting an olefin with hydrogen and carbon monoxide in the presence of a Group 8 to 10 metal-phosphine complex catalyst, comprising:
    (1) withdrawing a reaction solution having accumulated therein a high-boiling-point byproduct from a reaction zone and oxidizing by bringing the withdrawn reaction solution into contact with an oxygen-containing gas, and
    (2) after (1), mixing a poor solvent and hydrogen with the reaction solution, then crystallizing the Group 8 to 10 metal-phosphine complex catalyst by crystallization, and recovering the crystallized complex catalyst from the reaction solution,
    wherein the oxidation and the crystallization are performed under neutral to acidic conditions.

2. The aldehyde production method according to claim 1, wherein in the oxidation, an alkyl-substituted phosphine in the reaction solution is converted to an alkyl-substituted phosphine oxide.

3. The aldehyde production method according to claim 1, wherein in the oxidation, a cluster complex in the reaction solution is decomposed.

4. The aldehyde production method according to claim 2, wherein an oxidation ratio of the alkyl-substituted phosphine is from 5 to 80%.

5. The aldehyde production method according to claim 1, wherein the oxygen-containing gas is at least one selected from the group consisting of oxygen, air, and a gas obtained by adding nitrogen to air.

6. The aldehyde production method according to claim 1, wherein the oxidation is performed at 85 to 180° C.

7. The aldehyde production method according to claim 1, wherein the poor solvent is a mixture of water and an alcohol.

8. The aldehyde production method according to claim 1, wherein the complex catalyst recovered in the above step (2) is fed to the hydroformylation reaction zone.

9. The aldehyde production method according to claim 1, wherein the Group 8 to 10 metal is rhodium.

10. The aldehyde production method according to claim 1, wherein the oxidation is performed for 1 to 5 hours.

11. A method for producing an alcohol, comprising reacting an aldehyde produced by the method according to claim 1 with hydrogen.

12. A method for producing an alcohol, comprising producing an aldehyde by the method according to claim 1, followed by producing an alcohol from the aldehyde by reacting with hydrogen.

* * * * *